United States Patent
Xia et al.

(10) Patent No.: US 6,790,816 B2
(45) Date of Patent: Sep. 14, 2004

(54) HIGH OSMOLYTE CLEANING AND DISINFECTION METHOD AND SOLUTION FOR CONTACT LENSES

(75) Inventors: Erning Xia, Penfield, NY (US); Christine E. Soltys-Robitaille, Rochester, NY (US); Lisa C. Simpson, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/782,318

(22) Filed: Feb. 13, 2001

(65) Prior Publication Data

US 2002/0004466 A1 Jan. 10, 2002

(51) Int. Cl.$^7$ ................................................. C11D 3/48
(52) U.S. Cl. ........................ 510/112; 510/128; 510/134; 510/161; 510/163
(58) Field of Search ................................ 510/112, 128, 510/134, 161, 163

(56) References Cited

U.S. PATENT DOCUMENTS

| | | | |
|---|---|---|---|
| 2,979,528 A | 4/1961 | Lundsted ..................... 260/584 |
| 4,327,203 A | 4/1982 | Deichert et al. ............. 526/279 |
| 4,786,436 A | 11/1988 | Ogunbiyi et al. ........... 252/352 |
| 4,820,352 A * | 4/1989 | Riedhammer et al. ........ 134/30 |
| 5,037,647 A | 8/1991 | Chowhan et al. ............. 424/78 |
| 5,096,607 A | 3/1992 | Mowrey-McKee ......... 252/106 |
| 5,356,555 A | 10/1994 | Huth et al. ................. 252/106 |
| 5,401,431 A | 3/1995 | Nakagawa et al. ..... 252/174.21 |
| 5,409,546 A | 4/1995 | Nakagawa et al. ........... 134/42 |
| 5,449,442 A | 9/1995 | Yamada et al. ............. 204/130 |
| 5,487,788 A | 1/1996 | Kamiya et al. ................ 134/1 |
| 5,505,953 A | 4/1996 | Chowhan .................... 424/427 |
| 5,556,480 A | 9/1996 | Rontome et al. ............. 134/26 |
| 5,607,908 A | 3/1997 | Potini et al. ................. 510/115 |
| 5,630,884 A * | 5/1997 | Huth ............................ 134/27 |
| 5,648,074 A | 7/1997 | Park et al. .................. 424/94.2 |
| 5,654,262 A | 8/1997 | Desai et al. ................ 510/115 |
| 5,800,807 A | 9/1998 | Hu et al. .................. 424/78.04 |
| 5,820,696 A | 10/1998 | Kimura et al. ................ 134/42 |
| 5,858,937 A | 1/1999 | Richard et al. ............. 510/112 |
| 5,882,687 A | 3/1999 | Park et al. .................. 424/682 |
| 5,922,279 A | 7/1999 | Spooner ....................... 422/28 |
| 6,024,954 A | 2/2000 | Park et al. .................. 424/94.2 |
| 6,037,328 A * | 3/2000 | Hu et al. ....................... 514/23 |
| 6,096,138 A * | 8/2000 | Heiler et al. .................. 134/42 |
| 6,121,327 A | 9/2000 | Tsuzuki et al. ............. 514/642 |
| 6,143,244 A * | 11/2000 | Xia et al. ...................... 422/28 |
| 6,184,189 B1 | 2/2001 | Asgharian et al. .......... 510/112 |
| 6,309,658 B1 * | 10/2001 | Xia et al. .................... 424/405 |

FOREIGN PATENT DOCUMENTS

| WO | WO 96 06603 | 3/1996 | ......... A61K/31/135 |
|---|---|---|---|
| WO | WO 99 24543 | 5/1999 | ............ C11D/3/48 |

* cited by examiner

*Primary Examiner*—Brian P. Mruk
*Assistant Examiner*—Eisa Elhilo
(74) *Attorney, Agent, or Firm*—Robert Furr, Jr.; Denis A. Polyn; Rita D. Vacca

(57) ABSTRACT

Contact lens cleaning compositions comprising preserved surfactant-containing solutions of a poly(oxypropylene)-poly(oxyethylene) adduct of ethylene diamine having a molecular weight from about 7500 to as high as 27,000 wherein at least 40 weight percent of the adduct is poly(oxyethylene) hydrophilic units. The solutions are effective in removing protein/lipid tear film deposits on both hard and soft contact lenses while providing a prophylactic-like action in retarding the formation of subsequent tear film deposits. The compositions provide effective cleaning and conditioning action using both ambient and high temperature disinfection methods.

18 Claims, No Drawings

HIGH OSMOLYTE CLEANING AND DISINFECTION METHOD AND SOLUTION FOR CONTACT LENSES

BACKGROUND OF THE INVENTION

This invention relates generally to improved contact lens cleaning and conditioning solutions for removing and inhibiting build-up of tear film deposits and debris on lens surfaces.

In addition to the foregoing, the solutions of the present invention have improved versatility in being adaptable for most contact lens cleaning processes ranging from room temperature cleaning to high temperature disinfecting without adversely affecting the physical characteristics of the lenses.

When contact lenses are removed from the eyes, they lose water and retain on their surface a deposit or proteinaceous oily and sebaceous matter that, if not removed, greatly reduces wettability properties and optical clarity of the lenses. In the case of hard contact lenses fabricated from poly(methyl methacrylate), they are of such firmness the lenses can be treated with mechanical devices to remove deposits of contamination from their surfaces. Likewise, because hard contact lenses do not absorb appreciable amounts of water, the selection of cleaning agents is relatively non-critical. In many instances, use of even harsh disinfecting and cleaning agents on hard contact lenses does not create a problem.

However, because of the hydrophilic properties of soft contact lenses formulated from materials like poly(hydroxyethyl methacrylate), they do absorb more water than hard contact lenses. Consequently, greater care must be exercised in formulating cleansing solutions for soft contact lenses because materials in the solutions can be absorbed and concentrated in the lenses which in-turn can damage the lens and even injure the eyes of the user.

In many instances, solutions intended for hard contact lenses are generally not adaptable for use with soft contact lenses. This may be illustrated, for instance, in the case of hard contact lens solutions containing benzalkonium chloride or chlorobutanol, if used on soft contact lenses their important hydrophilic properties may be lost. Thus, in formulating contact lens care solutions, such as cleaning compositions, a number of factors need to be carefully weighed to assure total compatibility of the system in terms of functional efficaciousness, potential for damage to the lens and possible hazards to the wearer's eyes.

Multipurpose solutions that clean and disinfect contact lenses have been described in the literature. For example, U.S. Pat. Nos. 4,820,352 to Riedhammer et al. and 5,096,607 to Mowrey-McKee et al. disclose such solutions. More generally, contact lens solutions are disclosed in U.S. Pat. Nos. 5,356,555 to Huth et al., 5,401,431 to Nakagawa et al., 5,409,546 to Nakagawa et al., 5,449,442 to Yamada et al., 5,487,788 to Kamiya et al., 5,505,953 to Chowhan, 5,556,480 to Rontome et al., 5,607,908 to Potini et al., 5,630,884 to Huth, 5,648,074 to Park et al., 5,654,262 to Desai et al., 5,800,807 to Huth et al., 5,820,696 to Kimura et al., 5,858,937 to Richard et al., 5,922,279 to Spooner, 6,024,954 to Park et al., and 6,121,327 to Tsuzuki et al.

Most multipurpose solutions require the user to apply the solution to the contact lens and then to rub the contact lens, either between two fingertips or between a fingertip and the palm of the other hand. This step is known as "digital rubbing", and enhances cleaning. If a multipurpose solution were effective to clean and disinfect contact lenses without rubbing, maintaining contact lenses would be simpler and easier. Thus it would be desirable to provide a safe and effective solution for cleaning contact lenses that does not require digital rubbing.

SUMMARY OF THE INVENTION

The invention provides a no-rub cleaning and disinfecting solution comprising an effective amount of an antimicrobial, a cleaning solution together with an effective amount of an osmolyte that increases osmolality of the total solution without adversely affecting the antimicrobial efficacy of the cleaning and disinfecting solution.

More specifically, the invention provides a solution comprising an effective amount of an antimicrobial together with from about 0.01 to about 15 weight percent of poly(oxypropylene)-poly(oxyethylene) adduct of ethylene diamine having a molecular weight from about 7500 to about 27,000 wherein at least 40 weight percent of said adduct is poly(oxyethylene), together with a tonicity adjusting agent in sufficient concentration to promote cleaning efficacy without adversely affecting antimicrobial efficacy. Solutions disclosed herein will contain preservatives to maintain product sterility. In addition, pH of the cleaning and conditioning solutions, for example, may be adjusted by the addition of isotonic saline and buffering agents.

DESCRIPTION OF THE PREFERRED EMBODIMENTS

This invention relates to cleaning and conditioning solutions which are compatible for use with most contact lenses, including hard and soft lenses, as well as the newer hard gas permeable type contact lenses, such as described in U.S. Pat. No. 4,327,203. The term "soft contact lens" as used herein generally refers to those contact lenses that readily flex under small amounts of force and return to their original shape when that force is released. Typically, soft contact lenses are formulated from poly(hydroxyethyl methacrylate) which has been, in the preferred formulations, cross-linked with ethylene glycol dimethacrylate. For convenience, this polymer is generally known as PHEMA. Soft contact lenses are also made from silicon polymers cross-linked, for example, with dimethyl polysiloxane Conventional "hard contact lenses", which cover only the cornea of the eye, usually consists of poly(methyl methacrylate) cross-linked with ethylene glycol dimethacrylate.

The cleaning compositions of the present invention are particularly useful for removing and dispersing protein and lipid-containing film deposits that adhere to contact lens surfaces. In addition, the solutions of the immediate invention are also effective in conditioning lenses by providing a prophylactic-like action on lens surfaces retarding the rate and level of tear film development.

One embodiment of the aqueous contact lens cleaning and conditioning compositions comprises a block copolymer adduct of ethylene diamine non-ionic surfactant. The surfactant is a poly(oxypropylene)-poly(oxyethylene) block copolymer adduct of ethylene diamine having a molecular weight from about 7,500 to about 27,000, preferably from about 10,000 to about 20,000 where at least 40 weight percent, and more particularly, from about 40 to about 80 weight percent of the surfactant is poly(oxyethylene). More preferably, the poly(oxypropylene)-poly(oxyethylene) block copolymer adduct will have a molecular weight ranging from about 12,000 to about 19,000 where at least 60 weight percent, and more particularly, from about 60 to 80 weight percent of the adduct is poly(oxyethylene).

The foregoing surfactants are further described with methods for their manufacture in U.S. Pat. No. 2,979,528. They are also known by the generic name "poloxamine" and are commercially available from BASF-Wyandotte under the registered trademark "Tetronic". For convenience purposes, the surfactants employed in the cleaning and conditioning solutions disclosed herein will be referred to as Tetronic generally, and with a numerical suffix to identify a particular grade of material.

Grades of Tetronic surfactants available with molecular weights ranging from as low as 1650 to 27,000. Properties of each grade within the series vary depending on the percent of hydrophilic units poly(oxyethylene) and molecular weight of hydrophobic units poly(oxypropylene) in the adduct. While all members within the series exhibit wetting and detergency properties, it was discovered that only certain members are suitable for use in the cleaning and conditioning solutions disclosed herein, due to the wide variation in performance characteristics regulated by their hydrophilic-hydrophobic balance. The Tetronic surfactants found suitable are those capable of demonstrating maximum cleaning efficiency in dispersing both protein and lipid deposits at ambient and elevated temperatures at lowest solution concentration without trade-offs in lens compatibility and toxicity levels, i.e. maintaining lowest potential as an irritant to eye tissues. To illustrate, Tetronic surfactants having molecular weights of less than 7500 and having hydrophilic chains of about 10 weight percent poly(oxyethylene) units have the most effective detergent properties, but are substantially immiscible in aqueous solutions at 25° C. Consequently, Tetronic Series 701 through 1501 would be unsuitable for use in the aqueous contact lens cleaning solutions described herein. Similarly, solutions having only 20 weight percent hydrophilic units like Tetronic 702; 1102; 1302 and 1502 although miscible in aqueous medium and possessing superior detergency properties, they nevertheless, were found to have too high a potential for irritating eye tissues.

The present invention provides a no-rub method for dispersing both proteinaceous and lipid film deposits, as well as inhibiting film formation on contact lenses with little or no potential for irritation to eye tissues. The method employs a solution having improved cleaning efficacy as such that no physical agitation (i.e. digital rubbing) is required to effectively clean contact lenses.

The solution of the invention preferably employs the solid grades of Tetronic surfactant, particularly those having from about 60 to about 80 percent by weight poly(oxyethylene) hydrophilic units. These preferred embodiments include Tetronic 707; 1107 and 1307. Furthermore, because of their very hydrophilic properties, they remain in solution and do not become turbid.

The aqueous cleaning and conditioning solutions provide efficient performance at surfactant concentrations ranging from as little as 0.01 to about 15 weight percent. Greater concentrations may be used, but provide no added benefit and only increase the potential for irritating eye tissues. More preferably, the solutions of the subject invention will contain from about 0.1 to about 5 weight percent surfactant.

The method of the invention preferably provides both cleaning and disinfection in a single step. Accordingly, the solution of the invention preferably contains an antimicrobial agent. Examples of such agents include monomeric or polymeric biguanides, thimerosal, 1,5-pentanedial, alkyl triethanolamine, benzalkonium chloride, sorbic acid, phenylmercuric salts, e.g. nitrate, borate, acetate, chloride and mixtures thereof. Other antibacterial compounds and salts may be used, such as chlorhexidine (1,1'-hexamethylene-bis [5-(p-chlorophenyl)biguanide]) or its water soluble salts. Suitable salts of chlorhexidine are soluble in water at ambient temperature to the extent of at least 0.5 weight percent. These salts include the gluconate, isothionate (2-hydroxyethanesulfonate), formate, acetate, glutamate, succinamate, monodiglycollate, dimethanesulfonate, lactate, diisobutyrate and glucoheptonane. Typically, the antimicrobial will be used in an amount from about 0.001 to about 0.5 weight percent.

The preferred antimicrobials include biguanides and their salts. Salts of alexidine and chlorhexidine can be organic or inorganic, and are typically gluconates, nitrates, acetates, phosphates, sulphates, halides and the like. The most preferred antimicrobial agents are the polymeric quaternary ammonium salts used in ophthalmic applications and the biguanides. The antimicrobial agents preferred for use in the present invention are more preferably employed in the absence of mercury-containing compounds such as thimerosal.

A disinfecting amount of an antimicrobial agent is an amount that will at least partially reduce the microorganism population in the formulations employed. Preferably, a disinfecting amount is that which will reduce the microbial burden by two log orders in four hours and more preferably by one log order in one hour. Most preferably, a disinfecting amount is an amount which will eliminate the microbial burden on a contact lens when used in the regimen for the recommended soaking time (FDA Chemical Disinfection Efficacy Test—July, 1985 Contact Lens Solution Draft Guidelines). Typically, such agents are present in concentrations ranging from about 0.00001 to about 0.5 weight percent based on volume (w/v), and more preferably, from about 0.00003 to about 0.05% w/v.

The composition of the invention includes at least one tonicity-adjusting agent in concentration sufficient to increase the cleaning efficacy of the solution without adversely affecting the antimicrobial efficacy of the solution. Suitable tonicity adjusting agents include, but are not limited to metal halides such as magnesium, calcium, sodium and potassium chloride, mono-, di-, or polysaccharides, such as dextrose and trehalose, as well as amino acids such as lysine. Useful concentration ranges are shown below.

| Tonicity Adjusting Agent | Useful Concentration Range, Weight Percent. | Preferred Concentration Range, Weight Percent. | More Preferred Concentration Range, Weight Percent. |
| --- | --- | --- | --- |
| Sodium Chloride | 0.9–2.5 | 1.0–2.0 | 1.1–1.5 |
| Trehalose | 1.0–10.0 | 2.0–6.0 | 3.0–4.0 |
| Lysine | 1.0–5.0 | 2.0–4.0 | 2.5–3.5 |

These tonicity adjusting agents may be used individually or together in amounts ranging from about 0.01 to about 2.5 weight percent by volume (w/v) and preferably so that the final osmotic value of the cleaning and disinfecting solution has an osmotic value of more than 300 mOsm/kg, preferably more than 400 mOsm/kg and more preferably more than 500 mOsm/kg.

The tonicity-adjusting agents of the invention typically have a molecular weight of from about 30 to about 1000 grams per mole, preferably from about 40 to about 800 grams per mole, and more preferably from about 58 to about 500 grams per mole.

No further ingredients need be added to the preserved aqueous cleaning and conditioning solutions previously described. For example, the compositions of the present invention should be free or virtually free of agents which act specifically to thicken or increase the viscosity, or in other words, inhibit easy removal of the solution from lenses during the final rinsing step of a cleaning process. For purposes of the present invention, the expression "consisting essentially of" as used herein and in the claims means only those ingredients expressly recited plus inactive ingredients, including thickening agents in minor amounts which do not materially alter the viscosity of the solution, and excluding thickening agents which do materially alter the viscosity.

Notwithstanding the foregoing, in addition to the active ingredients previously described, tonicity agents, buffers and sequestering agents may be optionally employed. In this regard, added materials must be non-toxic and must not distort the lens. For example, inadvertently should the cleaning and conditioning solution not be washed from the lens after use, lens discomfort to the wearer can be avoided if the tonicity of the solution is modified to that of lacrimal fluids. Thus, the tonicity of the solution may be adjusted with 0.9 percent saline.

In order to maintain the pH of the cleaning and conditioning solutions within the range of about 6.5 to 7.8, suitable buffers may be added. Examples of useful buffering agents include, but are not limited to, alkali metal salts such as potassium or sodium carbonates, acetates, borates, phosphates, citrates and hydroxides, and weak acids such as acetic and boric acids. Preferred buffering agents include boric acid, sodium borate, potassium citrate, citric acid, sodium bicarbonate, including combinations of $Na_2PO_4$, $NaH_2PO_4$ and $KH_2PO_4$. Generally, buffers will be used in amounts ranging from about 0.01 to 2.5, and preferably, from 0.1 to 1.5 percent by weight/volume (w/v).

In addition to tonicity and buffering agents, in some instances it may be desirable to include sequestering agents to the cleaning and conditioning solutions in order to bind metal ions which might otherwise react with protein deposits and collect on the lens. Ethylenediaminetetraacetic acid (EDTA) and its salts (disodium) are preferred examples. They are usually added in amounts ranging from about 0.1 to about 2.0 weight percent.

The aqueous cleaning and conditioning solutions may be effectively used in removing and dispersing protein and lipid tear film deposits on both hard and soft type contact lenses by any of the well-recognized methods. For example, when the wearer of contact lenses removes them from the eyes, the lens may be rubbed with the cleaning solution followed by "cold" soaking at room temperature for a period ranging from about four to twelve hours. The lenses are then removed from the solution and replaced on the eyes. The wearer may optionally rinse the lenses in a preserved saline solution before replacing the lenses on the eyes.

When the cleaning process includes a rinsing step, however, the cleaning solution may contain higher concentrations of surfactant, e.g. 5 to 15 weight percent. However, the rinsing step may be omitted when, for example, the cleaning solution contains up to 0.5 weight percent of surfactant. In addition to the cold soaking method, the solutions disclosed herein are adaptable for use in other type of equipment such as ultrasonic cleaners. Furthermore, because the solutions are also stable when heated to temperatures in the range of 80° to 90° C. They are also adaptable for use with high temperature disinfecting methods. Typically, lenses are heated to 80° C. in a disinfecting unit containing the cleaning and conditioning solution for a time period of at least 10 minutes, removed and rinsed with isotonic saline.

The following specific examples demonstrate the compositions and methods of the instant invention. However, it is to be understood that these examples are for illustrative purposes only and do not purport to be wholely definitive as to conditions and scope.

EXAMPLE 1

An aqueous contact lens cleaning and conditioning solution was prepared having the following formulation:

| Ingredients | W/W % |
| --- | --- |
| Tetronic 1107 | 0.100 |
| Sodium Chloride | 0.675 |
| Boric Acid | 0.442 |
| Sodium Borate | 0.875 |
| Na2 EDTA | 0.100 |
| DYMED | 0.0001 |
| DD Water QS | 100.0 g |

The solution was prepared by dissolving the sodium borate in 800 ml of distilled water. The disodium EDTA was then added to the sodium borate solution, followed by dissolving the boric acid and sodium chloride therein. The Tetronic surfactant was subsequently added to the solution, but vigorous stirring was avoided to limit foam development in the solution. Thimerosal was added as a preservative and sufficient amount of distilled water to make 1 liter of solution. The solution may be sterilized by forcing through a 0.22 micron cellulose acetate filter by means of a peristaltic pump, or alternatively, by use of nitrogen gas under positive pressure. The solution had an osmolality of 320 mOsm/kg and was effective in removing tear film deposits from lenses.

EXAMPLE 2

An aqueous contact lens cleaning and conditioning solution was prepared with the following formulation:

| Ingredients | W/W % |
| --- | --- |
| Tetronic 1107 | 0.100 |
| Sodium Chloride | 0.675 |
| Boric Acid | 0.442 |
| Sodium Borate | 0.875 |
| $Na_2EDTA$ | 0.100 |
| DYMED | 0.0001 |
| Additional Sodium Chloride | 0.5% |
| DD Water QS | 100.0 g |

The pH of the solution of Example 2 was 7.0. The solution of Example 2 contains more NaCl than the solution of Example 1, to provide osmolality of 431 mOsm/kg.

EXAMPLE 3

An aqueous contact lens cleaning and conditioning solution was prepared with the following formulation:

| Ingredients | W/W % |
| --- | --- |
| Tetronic 1107 | 0.100 |
| Sodium Chloride | 0.675 |
| Boric Acid | 0.442 |
| Sodium Borate | 0.875 |
| $Na_2EDTA$ | 0.100 |
| DYMED | 0.0001 |

-continued

| Ingredients | W/W % |
| --- | --- |
| Trehelose | 3.0% |
| DD Water QS | 100.0 g |

The pH of the solution in Example 3 was 7.0. Trehelose was added to the solution to increase the osmolality to 393 mOsm/kg.

EXAMPLE 4

An aqueous contact lens cleaning solution was prepared having the following ingredients.

| Ingredients | W/W % |
| --- | --- |
| Tetronic 1107 | 0.100 |
| Sodium Chloride | 0.675 |
| Boric Acid | 0.442 |
| Sodium Borate | 0.875 |
| $Na_2EDTA$ | 0.100 |
| DYMED | 0.0001 |
| Lysine | 3.0% |
| DD Water QS | 100.0 g |

The pH of the solution of Example 4 was 7.0. Lysine was used in Example 4 to raise the osmolality to 614 mOsm/kg.

EXAMPLES 5–8

Examples 5–8 assess the effect of increasing the osmolarity (over 300 mOsm/kg) of novel solution products to assess passive (no-rub) cleaning capabilities. The osmolarity of each of the test solutions is included below. AcuVue brand soft contact lenses (commercially available from Johnson & Johnson, Incorporated were in-vitro deposited using a lysozyme deposition solution to assess the passive cleaning of three test solution products.

The following table represents the amount of lysozyme removed from the AcuVue lenses in an overnight soak, no rub regimen.

In-vitro Protein Deposition Profiles

| | Example 5 Evaluating Solution of Example 2 (NaCl) | Example 6 Evaluating Solution of Example 3 (Trehelose) | Example 7 Evaluating Solution of Example 4 (Lysine) | Example 8 Evaluating Solution of Example 1- Control |
| --- | --- | --- | --- | --- |
| Osmolality (mOsm/kg) | 431 | 393 | 614 | 320 |
| Total Lysozyme passively removed from lens (µg) | 96.2 ± 8.21 | 90.5 ± 3.65 | 125 ± 11.1 | 29.4 ± 3.17 |

* The values represent the average of six deposited AcuVue lenses.

The results surprisingly show that increasing the osmolality of the solution by adding NaCl, trehelose or lysine enhances the passive cleaning capabilities of a multipurpose cleaning/disinfecting solution.

Examples 5–8 used the following in-vitro deposition protocol.

a. In the preparation of the standard curve, dilutions are made from a 0.6 mg/ml stock of lysozyme in MOPS (3-N-morpholino)propanesulfonic acid and EDTA) buffer.

b. The protein deposition solution consists of 0.6 mg/ml Lysozyme in a MOPS buffer (pH 7.4, osmolarity 320 mOsm/kg). Six lenses were deposited for each test and control solution. For deposition, lenses were placed in 1.5 mls of the lysozyme mixture in a shaking water at 37° bath for 48 hours. After deposition, the lenses were rinsed with ReNu Saline in order to remove any residual deposition solution.

c. In order to determine the wavelength at which to run the samples, the original lysozyme deposition solution in MOPS was scanned by UV. The maximum absorbance was 280 nm which, became the wavelength at which the solutions were analyzed. The original deposition solution was analyzed for baseline lysozyme levels. In order to determine the amount of protein deposited, the solution after incubation with lens was analyzed. By difference, one can then ascertain the amount of lysozyme deposited on the lens.

d. To assess the passive cleaning efficacy (no rub) capabilities of the test and control solutions, the deposited lenses were placed in lens cases filled with the cleaning solutions and left to sit for 24 hours.

e. After the overnight soak, the lenses were removed and the solution analyzed at 280 nm for detection of lysozyme removed from the lens. The data represents the average values observed for the six deposited lenses.

Examples 5–8 evaluated the effect of increasing the osmolarity of a cleaning solution to provide superior passive cleaning capabilities. The osmolarity of each of the test solutions is included below. The in-vitro protein deposition studies of Examples 5–8 were performed on lysozyme deposited AcuVue lenses in order to assess the passive cleaning (no rub) capabilities of three solution products.

The results of Examples 5–8 indicate that the addition on NaCl, trehelose or lysine enhanced the passive cleaning capabilities of the control solution.

Examples 9–11 examined the disinfection efficacies of high osmolyte solutions. All disinfection tests are completed according to SOP 24-T008-02 (ISO Stand Alone Procedure for Disinfecting Products). The results are summarized in the following tables.

EXAMPLE 9

Sodium Chloride Formulation for Example 9:

| Ingredients | W/W % |
| --- | --- |
| Tetronic 1107 | 0.100 |
| Sodium Chloride | 1.175 |
| Boric Acid | 0.442 |
| Sodium Borate | 0.875 |
| $Na_2EDTA$ | 0.100 |
| PHMB | 0.00016 |
| DD Water | 100.0 g |

Microbiology Result for Example 9:

| Ingredients | | |
| --- | --- | --- |
| Staphylococcus aureus | 1 hour | 4.5 |
| | 4 hours | >4.6 |
| Pseudomonas aeruginosa | 1 hour | >4.6 |
| | 4 hours | >4.6 |

-continued

| Ingredients | | |
|---|---|---|
| *Serratia marcescens* | 1 hour | 3.0 |
| | 4 hours | >4.8 |
| *Candida albicans* | 1 hour | 0.6 |
| | 4 hours | 0.8 |
| *Fusarium solani* | 1 hour | 1.9 |
| | 4 hours | 2.6 |

Trehalose Formulation for Example 10:

| Ingredients | W/W % |
|---|---|
| Trehalose | 3.000 |
| Tetronic 1107 | 1.000 |
| Sodium Chloride | 0.675 |
| Boric Acid | 0.442 |
| Sodium Borate | 0.875 |
| Na₂EDTA | 1.100 |
| PHMB | 0.00016 |
| DD Water | 100.0 g |

Microbiology Result for Example 10:

| Ingredients | | |
|---|---|---|
| *Staphylococcus aureus* | 1 hour | 4.6 |
| | 4 hours | >4.4 |
| *Pseudomonas aeruginosa* | 1 hour | >4.6 |
| | 4 hours | >4.6 |
| *Serratia marcescens* | 1 hour | 4.8 |
| | 4 hours | >4.8 |
| *Candida albicans* | 1 hour | 3.6 |
| | 4 hours | 4.5 |
| *Fusarium solani* | 1 hour | 2.3 |
| | 4 hours | 3.0 |

Lysine Formulation for Example 11:

| Ingredients | W/W % |
|---|---|
| Lysine | 3.000 |
| Tetronic 1107 | 1.000 |
| Sodium Chloride | 0.675 |
| Boric Acid | 0.442 |
| Sodium Borate | 0.875 |
| Na₂EDTA | 0.100 |
| PHMB | 0.00016 |
| DD Water | 100.0 g |

Microbiology Result for Example 11:

| Ingredients | | |
|---|---|---|
| *Staphylococcus aureus* | 1 hour | 2.9 |
| | 4 hours | >4.6 |
| *Pseudomonas aeruginosa* | 1 hour | >4.6 |
| | 4 hours | >4.6 |
| *Serratia marcescens* | 1 hour | 3.2 |
| | 4 hours | >1.9 |

-continued

| Ingredients | | |
|---|---|---|
| *Candida albicans* | 1 hour | 1.2 |
| | 4 hours | 4.5 |
| *Fusarium solani* | 1 hour | 2.8 |
| | 4 hours | 3.5 |

What is claimed:

1. A no-rub cleaning and disinfecting solution comprising an effective amount of an antimicrobial, a cleaning solution together with an effective amount of 0.9 to about 2.5 weight percent of an osmolyte that increases osmolality of the total solution to a level higher than that of an eye's lacrimal fluids or an osmotic value greater than 300 mOsm/kg, to enhance the cleaning efficacy of the solution without adversely affecting the antimicrobial efficacy of the solution.

2. The solution of claim 1 wherein said osmolyte has a molecular weight of from about 30 to about 1000.

3. The solution of claim 2 wherein said osmolyte has a molecular weight of from about 40 to about 500.

4. The solution of claim 3 wherein said osmolyte has a molecular weight of from about 58 to about 500.

5. The solution of claim 1 further comprising two or more osmolytes having a weighted average molecular weight of from about 58 to about 500.

6. The solution of claim 1 having an osmolality of at least 400 mOsm/kg.

7. The solution of claim 6 having an osmolality of at least 500 mOsm/kg.

8. An aqueous solution for effectively cleaning contact lenses without rubbing comprising:

a) from about 0.01 to about 15 weight percent of a poly(oxypropylene)-poly(oxyethylene) adduct of ethylene diamine having a molecular weight from about 7500 to about 27,000 wherein at least 40 weight percent of said adduct is poly(oxyethylene);

b) an effective amount of at least one antimicrobial; and c) at least one osmolyte adjusting agent in concentration of 0.9 to about 2.5 weight percent sufficient to increase osmolality of the total solution to a level higher than that of an eye's lacrimal fluids or an osmotic value greater than 300 mOsm/kg, to enhance the cleaning properties of the solution without adversely affecting its antimicrobial efficacy.

9. The solution of claim 8 wherein said osmolyte has a molecular weight of from about 30 to about 1000.

10. The solution of claim 9 wherein said osmolyte has a molecular weight of from about 40 to about 800.

11. The solution of claim 10 wherein said osmolyte has a molecular weight of from about 58 to about 500.

12. The solution of claim 8 wherein the molecular weight of the adduct is from about 10,000 to about 20,000 and from about 40 to about 80 weight percent of the adduct is poly(oxyethylene).

13. The solution of claim 12 wherein the molecular weight of the adduct is from about 12,000 to about 19,000 and from about 60 to about 80 weight percent of the adduct is poly(oxyethylene).

14. The solution of claim 13 wherein the adduct is present in an amount from about 0.1 to about 5 weight percent.

15. The solution of claim 8, including a buffering agent.

16. An aqueous composition for inhibiting the formation of tear film deposits on contact lenses, consisting essentially of:
   a) at least 0.01 weight percent of poly(oxypropylene)-poly(oxyethylene) adduct of ethylene diamine having a molecular weight from about 10,000 to about 20,000 wherein at least 40 weight percent of said adduct is poly(oxyethylene);
   b) a germicidal agent in a sufficient amount to preserve the sterility of the composition; and
   c) an osmolyte adjusting agent in concentration of 0.9 to about 2.5 weight percent sufficient to increase osmolality of the total solution to a level higher than that of an eye's lacrimal fluids or an osmotic value greater than 300 mOsm/kg, to enhance the cleaning efficacy of the solution without inhibiting the antimicrobial efficacy of the solution.

17. The composition of claim 16 wherein the molecular weight of the adduct is from about 12,000 to about 19,000 and at least 60 weight percent of the adduct is poly(oxyethylene).

18. A no-rub method for cleaning and disinfecting contact lenses comprising the steps of exposing said contact lenses to an aqueous solution containing an effective amount of an antimicrobial, an effective amount of a cleaning agent and an effective amount of 0.9 to about 2.5 weight percent of an osmolyte that increases osmolality of the total solution to a level higher than that of an eye's lacrimal fluids or an osmotic value greater than 300 mOsm/kg, to enhance the cleaning efficacy of the solution without adversely affecting the antimicrobial efficacy of the solution.

* * * * *